United States Patent
Dandekar et al.

(10) Patent No.: US 7,019,185 B2
(45) Date of Patent: Mar. 28, 2006

(54) AROMATIC ALKYLATION PROCESS

(75) Inventors: Ajit Bhaskar Dandekar, Fairfax, VA (US); John P. McWilliams, Swedesboro, NJ (US); Thomas Francis Degnan, Jr., Moorestown, NJ (US); Michael Hryniszak, Bordentown, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 476 days.

(21) Appl. No.: 10/313,278

(22) Filed: Dec. 6, 2002

(65) Prior Publication Data

US 2004/0111001 A1 Jun. 10, 2004

(51) Int. Cl.
*C07C 2/68* (2006.01)
*C07C 2/64* (2006.01)

(52) U.S. Cl. ....................... 585/467; 585/446
(58) Field of Classification Search ............... 585/446, 585/467
See application file for complete search history.

(56) References Cited

U.S. PATENT DOCUMENTS

| | | | |
|---|---|---|---|
| 3,751,504 A | 8/1973 | Keown et al. | |
| 4,016,218 A | 4/1977 | Haag et al. | |
| 4,439,409 A | 3/1984 | Puppe et al. | |
| 4,547,605 A | 10/1985 | Kresge et al. | |
| 4,826,667 A | 5/1989 | Zones et al. | |
| 4,891,458 A | 1/1990 | Innes et al. | |
| 4,954,325 A | 9/1990 | Rubin et al. | |
| 4,992,606 A | 2/1991 | Kushnerick et al. | |
| 5,149,894 A * | 9/1992 | Holtermann et al. | 585/467 |
| 5,236,575 A | 8/1993 | Bennett et al. | |
| 5,250,277 A | 10/1993 | Kresge et al. | |
| 5,258,565 A | 11/1993 | Kresge et al. | 585/467 |
| 5,334,795 A | 8/1994 | Chu et al. | |
| 5,362,697 A | 11/1994 | Fung et al. | |
| 5,493,065 A | 2/1996 | Cheng et al. | 585/467 |
| 5,600,048 A * | 2/1997 | Cheng et al. | 585/449 |
| 6,077,498 A | 6/2000 | Diaz Cabanas et al. | |
| 6,111,157 A * | 8/2000 | Hendriksen et al. | 585/467 |

FOREIGN PATENT DOCUMENTS

| | | |
|---|---|---|
| EP | 293 032 | 7/1993 |
| WO | WO 97/17290 | 5/1997 |
| WO | WO 01/21562 A1 * | 2/2001 |

OTHER PUBLICATIONS

Database of Zeolite Structures, 2000 International Zeolite Association.*

* cited by examiner

*Primary Examiner*—Walter D. Griffin
*Assistant Examiner*—In Suk Bullock
(74) *Attorney, Agent, or Firm*—D. M. Tyus; L. A. Kubena

(57) ABSTRACT

In a method for producing monoalkylated aromatic compounds, an aromatic feed is contacted with an alkylating agent in the presence of a catalyst comprising a molecular sieve having an X-ray diffraction pattern including d-spacing maxima at 12.4±0.25, 6.9±0.15, 3.57±0.07, and 3.42±0.07 Angstrom. The catalyst also contains at least one metal cation selected from Groups 1–4 and 7–16 of the Periodic Table of Elements, wherein the metal cation is present in an amount of at least 0.5% by weight of the catalyst, whereby selectivity of the catalyst to produce monoalkylates over polyalkylates is improved as compared with the identical catalyst but without the metal cation present.

15 Claims, No Drawings

AROMATIC ALKYLATION PROCESS

FIELD

The present invention relates to an aromatic alkylation process and, in particular, an aromatic alkylation process for the production of ethylbenzene and cumene.

BACKGROUND

Ethylbenzene and cumene are valuable commodity chemicals that are used industrially for the production of styrene monomers and co-production of phenol and acetone respectively. Ethylbenzene may be produced by a number of different chemical processes but one process that has achieved a significant degree of commercial success is the vapor phase alkylation of benzene with ethylene in the presence of a solid, acidic zeolite catalyst, such as ZSM-5. Examples of such ethylbenzene production processes are described in U.S. Pat. Nos. 3,751,504, 4,547,605, and 4,016,218. U.S. Pat. No. 4,992,606 describes the use of MCM-22 in the alkylation of aromatic compounds, such as benzene, with short chain alkylating agents, such as ethylene and propylene.

More recently, focus has been directed at liquid phase processes for producing ethylbenzene from benzene and ethylene since liquid phase processes operate at a lower temperature than their vapor phase counterparts and hence tend to result in lower yields of by-products. For example, U.S. Pat. No. 4,891,458 describes the liquid phase synthesis of ethylbenzene with zeolite beta, whereas U.S. Pat. No. 5,334,795 describes the use of MCM-22 in the liquid phase synthesis of ethylbenzene.

Existing processes for producing ethylbenzene, however, inherently produce polyalkylated species as well as the desired monoalkylated product. It is therefore normal to transalkylate the polyalkylated species with benzene to produce additional ethylbenzene either by recycling the polyalkylated species to the alkylation reactor or by feeding the polyalkylated species to a separate transalkylation reactor. The conversion of polyalkylated back to monoalkylated product is therefore an additional step that that adds complexity and cost to the process. Further, the quantities of impurities and heavy byproducts per unit of monoalkylate formed are typically higher in this recycle step than in the primary alkylation step.

There is a need for a process that reduces the amount of polyalkylates formed in the initial conversion of aromatics with an alkylating agent into monoalkylates, thereby reducing the amount of polyalkylates to be converted into monoalkylates and subsequent by-products inherent in that process.

SUMMARY

In one aspect, the present invention resides in a process for producing monoalkylated aromatic compounds comprising contacting an aromatic feed with an alkylating agent in the presence of a catalyst comprising a molecular sieve having an X-ray diffraction pattern including d-spacing maxima at 12.4±0.25, 6.9±0.15, 3.57±0.07, and 3.42±0.07 Angstrom and at least one metal cation selected from Groups 1–4 and 7–16 of the Periodic Table of Elements, wherein the metal cation is present in an amount of at least 0.5% by weight of the catalyst, whereby selectivity of the catalyst to produce monoalkylates over polyalkylates is improved as compared with the identical catalyst but without the metal cation present.

Typically, the metal cation is present in an amount between about 0.5% and 5.0% by weight of the catalyst.

In one embodiment, the molecular sieve is selected from MCM-22, PSH-3, SSZ-25, ERB-1, ITQ-1, ITQ-2, MCM-36, MCM-49 and MCM-56.

In one embodiment, the metal cation is selected from Groups 1–4 and 12–16 of the Periodic Table of Elements. In another embodiment, the metal cation is selected from Groups 7–11 of the Periodic Table of Elements.

The aromatic feed may comprise benzene and the alkylating agent may comprise ethylene or propylene.

DESCRIPTION

The present invention is directed to a process for producing a monoalkylated aromatic compound in high concentration, such as ethylbenzene or cumene, by reacting an aromatic feedstock, such as benzene, with an alkylating agent, such as ethylene or propylene, in the presence of an MCM-22 family catalyst containing at least 0.5% by weight of at least one metal cation from Groups 1–4 or 7–16 of the Periodic Table of the Elements (ACS version).

The term "aromatic" in reference to the alkylatable compounds which are useful herein is to be understood in accordance with its art-recognized scope which includes alkyl substituted and unsubstituted mono- and polynuclear compounds. Compounds of an aromatic character that possess a heteroatom are also useful provided they do not act as catalyst poisons under the reaction conditions selected.

Suitable aromatic hydrocarbons include benzene, naphthalene, anthracene, naphthacene, perylene, coronene, and phenanthrene, with benzene being preferred. Generally the alkyl groups which can be present as substituents on the aromatic compound contain from 1 to about 22 carbon atoms and usually from about 1 to 8 carbon atoms, and most usually from about 1 to 4 carbon atoms.

The alkylating agents which are useful in the process of this invention generally include any aliphatic or aromatic organic compound having one or more available alkylating aliphatic groups capable of reaction with the alkylatable aromatic compound, for example with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt % | Mole % |
| --- | --- | --- |
| Ethane | 3.3 | 5.1 |
| Ethylene | 0.7 | 1.2 |

-continued

|  | Wt % | Mole % |
|---|---|---|
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products which may be obtained from the process of the invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes.

The alkylation process is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition, under effective alkylation conditions. Such conditions include a temperature of from about 0° C. to about 500° C., for example between about 50° C. and about 350° C., a pressure of from about 0.2 to about 250 atmospheres (20 to 25250 kPa), for example from about 5 to about 100 atmospheres (500 to 10100 kPa), a molar ratio of alkylatable aromatic compound to an alkylating agent of from about 0.1:1 to about 50:1, for example from about 0.5:1 to about 10:1, and a feed weight hourly space velocity (WHSV) of between about 0.1 and 500 hr$^{-1}$, for example between 0.5 and 100 hr$^{-1}$.

The reactants can be in either the vapor phase or partially or completely in the liquid phase and can be neat, i.e., free from intentional admixture or dilution with other material, or they can be brought into contact with the zeolite catalyst composition with the aid of carrier gases or diluents such as, for example, hydrogen or nitrogen.

When benzene is alkylated with ethylene to produce ethylbenzene, the alkylation reaction may be carried out in the liquid phase under conditions including a temperature between 300° and 600° F. (about 150° and 316° C.), for example between 400° F. and 500° F. (about 205° C. and 260° C.), a pressure up to about 200 atmospheres (20875 kPa), for example between 400 and 800 psig (2860 and 5600 kPa), a feed weight hourly space velocity between about 0.1 and 20 hr$^{-1}$, for example between 1 and 6 hr$^{-1}$, based on the ethylene feed, and a molar ratio of the benzene to the ethylene in the alkylation reactor from 1:1 to 30:1, for example from about 1:1 to 10:1.

When benzene is alkylated with propylene to produce cumene, the reaction may also take place under liquid phase conditions including a temperature of up to about 250° C., for example up to about 150° C., for example from about 10° C. to about 125° C.; a pressure of about 250 atmospheres or less, for example from about 1 to about 30 atmospheres; a molar ratio of the benzene to the propylene of from about 1:1 to about 30:1, for example from about 1:1 to about 10:1, and a feed weight hourly space velocity of from about 5 hr$^{-1}$ to about 250 hr$^{-1}$, for example from 5 hr$^{-1}$ to 50 hr$^{-1}$, based on benzene feed.

The alkylation catalyst of the present invention is a crystalline molecular sieve having an X-ray diffraction pattern including d-spacing maxima at 12.4±0.25, 6.9±0.15, 3.57±0.07, and 3.42±0.07 Angstrom. The X-ray diffraction data used to characterize the molecular sieve material used in the catalyst of the invention are obtained by standard techniques using the K-alpha doublet of copper as the incident radiation and a diffractometer equipped with a scintillation counter and associated computer as the collection system.

Materials having the required X-ray diffraction pattern are sometimes referred to as molecular sieves of the MCM-22 family and include MCM-22 (described in U.S. Pat. No. 4,954,325), PSH-3 (described in U.S. Pat. No. 4,439,409), SSZ-25 (described in U.S. Pat. No. 4,826,667), ERB-1 is described in European Patent No. 0293032, ITQ-1 is described in U.S. Pat. No. 6,077,498, ITQ-2 is described in International Patent Publication WO97/17290, MCM-36 (described in U.S. Pat. No. 5,250,277), MCM-49 (described in U.S. Pat. No. 5,236,575) and MCM-56 (described in U.S. Pat. No. 5,362,697). The molecular sieve can be combined in a conventional manner with an oxide binder, such as alumina, such that the final alkylation catalyst contains between 2 and 80 wt % sieve.

The molecular sieve catalyst employed in the process of the invention is modified by the addition of one or more metal cations from Groups 1 through 4 and Groups 7 though 16 of the Periodic Table of Elements, such that the catalyst contains at least 0.5% by weight of such metal cation(s), for example from about 0.5% to about 5% by weight of such metal cation(s). In one embodiment, the catalyst contains from about 1% to about 4% by weight of the metal cation(s).

It is to be appreciated that the molecular sieve used in the process of the invention will, when initially synthesized, normally contain alkali metal cations in addition to any organic directing agent used in its synthesis. However, the amount of alkali metal cation in the as-synthesized material is normally very small and is significantly less than 0.5% by weight of the molecular sieve material. In fact, the alkali metal cation, together with any organic directing agent, will normally be removed from the as-synthesized material by methods well-known in the art so that the molecular sieve can be converted to the active hydrogen form. In accordance with the invention, the required cation or cations from Groups 1 through 4 and Groups 7 though 16 can then be incorporated into the hydrogen form molecular sieve in an amount in excess of the alkali metal cation present in the as-synthesized material. It is, however, also possible to retain the alkali metal cation present in the as-synthesized molecular sieve and incorporate additional cations from Groups 1 through 4 and Groups 7 though 16 in an amount sufficient to bring the overall cation content to the minimum value of 0.5% by weight of the catalyst.

In one embodiment, the metal cation is selected from Groups 1–4 and 12–16, in which case typical cations include K, Mg, Ca, Ba, B, Al, Ga, Sn, Zn, La, Ce, Ti, Zr, V, Mo, and W. In another embodiment, the metal cation is selected from Groups 7–11, in which case typical cations include Mn, Re, Fe, Ru, Co, Pd, Pt, Cu, and Ag.

There are a variety of ways to incorporate the metal cations into the catalyst. Examples well known in the art include wet impregnation and ion exchange.

Surprisingly, it is found that the incorporating at least 0.5 wt % metal cations into the molecular sieve catalyst of the invention enhances the selectivity of the catalyst to produce monoalkylates over polyalkylates as compared with the identical catalyst but without the metal cation present. If the concentration of metal cation is less than 0.5 wt %, the increased mono-selectivity is difficult to detect. Moreover, although the upper limit on metal cation content is not critical for mono-selectivity, if the cation content becomes too high the loss in activity of the catalyst can be detrimental to alkylate yield.

Although the alkylation process of the invention is highly selective toward the production of monoalkylated aromatic products, the effluent from the alkylation reaction will normally contain some polyalkylated products, as well as unreacted aromatic feed and the desired monoalkylated species. The unreacted aromatic feed is normally recovered by distillation and recycled to the alkylation reactor. The bottoms from the benzene distillation are further distilled to separate monoalkylated product from any polyalkylated products and other heavies. Depending on the amount of polyalkylated products present in the alkylation reaction effluent, it may be desirable to transalkylate the polyalkylated products with additional aromatic feed to maximize the production of the desired monoalkylated species. However, if the molar ratio of aromatic feed to alkylating agent in the alkylation stage is sufficiently high (such as above 5:1), it may be possible to obviate the need for a separate transalkylation step. In any event, the amount polyalkylated product requiring transalkylation is significantly reduced using the catalyst of the invention as compared with a conventional catalyst without the metal cation addition.

Where the polyalkylated products separated from the alkylation reactor effluent are transalkylated with additional aromatic feed, this is typically effected in a transalkylation reactor, separate from the alkylation reactor, over a suitable transalkylation catalyst, such as an MCM-22 family catalyst, zeolite beta, zeolite Y, or mordenite. The transalkylation reaction is typically conducted under at least partial liquid phase conditions such that the polyalkylated aromatics react with the additional aromatic feed to produce additional monoalkylated product. Suitable transalkylation conditions include a temperature of 100° to 260° C., a pressure of 10 to 50 barg (1100–5100 kPa), a weight hourly space velocity of 1 to 15 on total feed, and benzene/polyalkylated benzene weight ratio 0.5:1 to 6:1.

When the polyalkylated aromatics are polyethylbenzenes and are reacted with benzene to produce ethylbenzene, the transalkylation conditions preferably include a temperature of 220° to 260° C., a pressure of 20 to 30 barg, weight hourly space velocity of 2 to 10 based on total feed and benzene/PEB weight ratio 1:1 to 6:1.

When the polyalkylated aromatics are polyisopropylbenzenes and are reacted with benzene to produce cumene, the transalkylation conditions preferably include a temperature of 100° to 200° C., a pressure of 20 to 30 barg, weight hourly space velocity of 1 to 15 on total feed and benzene/PIPB weight ratio 1:1 to 6:1.

The effluent from the transalkylation reactor is blended with alkylation reactor effluent and the combined stream distilled to separate the desired monoalkylated product.

The following examples are given for illustrative purposes and do not limit the scope of the invention:

EXAMPLE 1

The first example compares the results of impregnating an MCM-22 catalyst with a metal ion chosen from Groups 1–4 and 12–16.

An MCM-22 catalyst for use as a base comparison was prepared by extruding 65 wt % MCM-22 crystal with 35 wt % alumina into 1/16" (1.6 mm) extrudate. One gram of the catalyst was charged to an isothermal well-mixed Parr autoclave reactor along with a mixture comprising of benzene (195 g) and ethylene (20 g). The reaction was carried out at 220° C. (428° F.) and 3890 kPa (550 psig) for 4 hours. A small sample of the product was withdrawn at regular intervals and analyzed by gas chromatography. The catalyst performance was assessed by a kinetic activity second order rate constant based on ethylene conversion and ethylbenzene selectivity at 100% ethylene conversion (shown in Table 2).

An impregnated sample was prepared by taking a measured amount of a metal containing salt (amounts depending on example are given in Table 1) that was dissolved in approximately 50 grams of distilled water to yield a solution of variable pH. The resulting solution was used to impregnate 50 grams of a fresh sample of MCM-22 using a wet impregnation method. The impregnated catalyst was dried at 120° C. (250° F.) for 12 hours in air followed by calcination at 360°–540° C. (680°–1000° F.) in flowing air for 4 hours.

TABLE 1

| Sample | Metal Containing Salt | Amount used in Grams | Metal Cation (wt % of Catalyst) |
|---|---|---|---|
| 1 | $KNO_3$ | 0.64 | 1.6 |
| 2 | $Mg(NO_3)_2$ | 5.28 | 1.0 |
| 3 | $Ga(NO_3)_3$ | 10.6 | 1.0 |
| 4 | $Al(NO_3)_3$ | 13.92 | 2.0 |
| 5 | $Zn(NO_3)_2$ | 1.82 | 0.8 |
| 6 | $Ce(NO_3)_3$ | 1.24 | 0.8 |
| 7 | $La(NO_3)_3$ | 1.24 | 0.8 |
| 8 | $ZrO(NO_3)_2 \cdot xH_2O$ | 1.02 | 1.6 |
| 9 | $(NH_4)_6Mo_7O_{24} \cdot 4H_2O$ | 5.2 | 0.8 |

One gram of the final catalyst was evaluated for benzene alkylation with ethylene according to the procedure described in the MCM-22 base preparation. Catalyst performance is compared with unmodified MCM-22 in Table 2. It will be seen that the metal modification decreased the amount of polyalkylated species in the reaction product.

TABLE 2

| Sample | Activity Parameter | DiEB/EB (wt %) | TriEB/EB (wt %) | Reduction in DiEB (wt %) | Reduction in TriEB (wt %) |
|---|---|---|---|---|---|
| Base | 41 | 8.5 | 0.35 | — | — |
| 1 (K) | 20 | 4.6 | 0.1 | 45.8 | 71.4 |
| 2 (Mg) | 17 | 4.6 | 0.1 | 45.8 | 71.4 |
| 3 (Ga) | 40 | 6.8 | 0.22 | 20.0 | 37.1 |
| 4 (Al) | 36 | 7.0 | 0.25 | 17.6 | 28.5 |
| 5 (Zn) | 30 | 5 | 0.1 | 41.1 | 71.4 |
| 6 (Ce) | 30 | 5.6 | 0.15 | 34.1 | 57.1 |
| 7 (La) | 34 | 5.1 | 0.1 | 40.0 | 71.4 |
| 8 (Zr) | 30 | 6 | 0.16 | 29.4 | 54.2 |
| 9 (Mo) | 5 | 5 | 0.1 | 41.1 | 71.4 |

EXAMPLE 2

The second example compares the results of impregnating an MCM-22 catalyst with a metal ion chosen from Groups 7–11.

An MCM-22 catalyst to be used as a base comparison was prepared in the same way as the base sample in Example 1.

An impregnated sample was prepared by taking measured amounts of a metal containing salt (amounts depending on example are given in Table 3) that was dissolved in approximately 50 grams of distilled water to yield a solution of variable pH. The resulting solution was used to impregnate 50 grams of a fresh sample of MCM-22 using a wet impregnation method. The impregnated catalyst was dried at 120° C. (250° F.) for 12 hours in air followed by calcination at 360° C. (680° F.) in flowing air for 4 hours.

TABLE 3

| Sample | Metal Containing Salt | Amount used in Grams | Metal Cation (wt % of Catalyst) |
|---|---|---|---|
| 1 | $CuNO_3$ | 1.9 | 1.0 |
| 2 | $AgNO_3$ | 0.63 | 0.8 |
| 3 | $Mn(NO_3)_2 \cdot 6H_2O$ | 1.65 | 0.8 |
| 4 | $NH_4ReO_7$ | 0.58 | 0.8 |
| 5 | $Fe(NO_3)_3$ | 3.62 | 1.0 |
| 6 | $Co(NO_3)_2$ | 1.98 | 0.8 |
| 7 | $(NH_3)_6Pt(NO_3)_2$ | 12.6 | 1.0 |

One gram of the final catalyst was evaluated for benzene alkylation with ethylene according to the procedure described in the MCM-22 base preparation. Catalyst performance is compared with unmodified MCM-22 in Table 4. As in the case of Example 1, it will be seen that the metal modification decreased the amount of polyalkylated species in the reaction product.

TABLE 4

| Sample | Activity Parameter | DiEB/EB (wt %) | TriEB/EB (wt %) | Reduction in DiEB (wt %) | Reduction in TriEB (wt %) |
|---|---|---|---|---|---|
| Base | 41 | 8.5 | 0.35 | — | — |
| 1 (Cu) | 28 | 4.8 | 0.1 | 43.5 | 71.4 |
| 2 (Ag) | 38 | 6.7 | 0.2 | 21.1 | 42.8 |
| 3 (Mn) | 32 | 5.1 | 0.1 | 40.0 | 71.4 |
| 4 (Re) | 37 | 5.7 | 0.12 | 32.9 | 65.7 |
| 5 (Fe) | 32 | 5.9 | 0.15 | 30.5 | 57.1 |
| 6 (Co) | 10 | 5.7 | 0.12 | 32.9 | 65.7 |
| 7 (Pt) | 20 | 6.0 | 0.12 | 29.4 | 65.7 |

EXAMPLE 3

The third example compares the results of impregnating an MCM-22 catalyst with copper in varying amounts.

The MCM-22 catalyst used as the base comparison was prepared in the same way as the base sample in Example 1.

An impregnated sample was prepared by taking measured amounts of copper nitrate (amounts depending on example are given in Table 5) that was dissolved in approximately 50 grams of distilled water to yield a solution of variable pH. The resulting solution was used to impregnate 50 grams of a fresh sample of MCM-22 using a wet impregnation method. The impregnated catalyst was dried at 120° C. (250° F.) for 12 hours in air followed by calcination at 360° C. (680° F.) in flowing air for 4 hours.

TABLE 5

| Sample | Metal Containing Salt | Amount used in Grams | Metal Cation (wt % of Catalyst) |
|---|---|---|---|
| 1 | $CuNO_3$ | 0.38 | 0.2 |
| 2 | $CuNO_3$ | 0.95 | 0.5 |
| 3 | $CuNO_3$ | 1.52 | 0.8 |
| 4 | $CuNO_3$ | 1.9 | 1.0 |
| 5 | $CuNO_3$ | 3.8 | 2.0 |
| 6 | $CuNO_3$ | 9.5 | 5.0 |
| 7 | $CuNO_3$ | 19.0 | 10.0 |

One gram of the final catalyst was evaluated for benzene alkylation with ethylene according to the procedure described in the MCM-22 base preparation. Catalyst performance is compared with unmodified MCM-22 in Table 6.

TABLE 6

| Sample | Activity Parameter | DiEB/EB (wt %) | TriEB/EB (wt %) | Reduction in DiEB (wt %) | Reduction in TriEB (wt %) |
|---|---|---|---|---|---|
| Base | 41 | 8.5 | 0.35 | — | — |
| 1 (0.2% Cu) | 40 | 8.5 | 0.34 | — | 2.9 |
| 2 (0.5% Cu) | 35 | 5.0 | 0.12 | 41.5 | 65.7 |
| 3 (0.8% Cu) | 32 | 5.2 | 0.1 | 38.8 | 71.4 |
| 4 (1.0% Cu) | 28 | 4.8 | 0.1 | 43.5 | 71.4 |
| 5 (2.0% Cu) | 24 | 4.8 | 0.1 | 43.5 | 71.4 |
| 6 (5.0% Cu) | 12 | 4.9 | 0.1 | 42.4 | 71.4 |
| 7 (10% Cu) | 2 | 4.8 | 0.1 | 43.5 | 71.4 |

It will be seen from FIG. 6 that the catalyst containing only 0.1 wt % copper exhibited essentially the same monoalkylate selectivity as the unmodified catalyst, whereas the catalyst containing 0.5 wt % copper produced 41 wt % less diethylbenzene and 66 wt % less triethylbenzene than the unmodified catalyst. It will also be seen that increasing the copper level above 5 wt % produced little further improvement in monoselectivity and was accompanied by a significant decline in the activity of the catalyst.

EXAMPLE 4

One gram each of six representative metal-impregnated MCM-22 catalyst samples, selected from those described in Examples 1 and 2, were evaluated for benzene alkylation with propylene to cumene according to a procedure described below.

One gram of the catalyst was charged to an isothermal well-mixed Parr autoclave reactor along with a mixture comprised of benzene (156 g) and propylene (28 g). The reaction was carried out at 130° C. (266° F.) and 2070 kPa (300 psig) for 4 hours. A small sample of the product was withdrawn at regular intervals and analyzed by gas chromatography. The catalyst performance was assessed by a kinetic activity second order rate constant based on propylene conversion and cumene selectivity at 100% cumene conversion (shown in Table 7).

TABLE 7

| Sample | Metal Cation (wt % of Catalyst) | Activity Parameter | DiEB/EB (wt %) | TriEB/EB (wt %) | Reduction in DiEB (wt %) | Reduction in TriEB (wt %) |
|---|---|---|---|---|---|---|
| Base | — | 80 | 17.1 | 1.6 | — | — |
| 1 (Cu) | 1.0 | 65 | 13.1 | 0.9 | 23.4 | 43.8 |
| 2 (Pt) | 1.0 | 55 | 11.5 | 0.7 | 32.7 | 56.3 |
| 3 (Fe) | 1.0 | 40 | 13.7 | 1.1 | 19.9 | 31.3 |
| 4 (Al) | 2.0 | 62 | 13.4 | 1.1 | 21.6 | 31.3 |
| 5 (Mn) | 0.8 | 60 | 12.1 | 0.8 | 29.2 | 50.0 |
| 6 (La) | 0.8 | 61 | 12.2 | 0.8 | 40.2 | 50.0 |

The invention claimed is:

1. A method for producing monoalkylated aromatic compounds, comprising the step of contacting an aromatic feed with an alkylating agent in the presence of a catalyst, to produce a monalkylated aromatic compound and polyalkylated products, said catalyst comprising:
   (a) a MCM-22 molecular sieve; and
   (b) at least one metal cation selected from Groups 1 to 3 of the Periodic Table of Elements, said metal cation present in said catalyst in an amount at least 0.5 percent by weight of the catalyst;
wherein said catalyst produces a reduced amount of polyalkylated products as compared to an identical catalyst not having said amount of metal cation present.

2. The method of claim 1, wherein the metal cation is K, Mg, or La.

3. The method of claim 1, wherein the monoalkylated aromatic compound is ethylbenzene, the alkylating agent is ethylene, and the aromatic feed is benzene.

4. The method of claim 1, where the monoalkylated aromatic compound is cumene, the alkylating agent is propylene, and the aromatic feed is benzene.

5. A method for producing ethylbenzene, comprising the step of contacting a benzene feed with ethylene in the presence of a catalyst, to produce ethylbenzene and polyethylbenzenes, said catalyst comprising:
   (a) a MCM-22 molecular sieve; and
   (b) at least one metal cation selected from K, La and Mg, said metal cation present in said catalyst in an amount at least 0.5 percent by weight of the catalyst;
wherein said catalyst produces a reduced amount of polyethylbenzenes as compared to an identical catalyst not having said amount of metal cation present.

6. A method for producing monoalkylated aromatic compounds, comprising the step of contacting an aromatic feed with an alkylating agent in the presence of a catalyst, to produce a monalkylated aromatic compound and polyalkylated products, said catalyst comprising:
   (a) a MCM-22 molecular sieve; and
   (b) at least one metal cation selected from Ag, Ca, Cu, Fe, Mn, Pt and Re, said metal cation present in said catalyst in an amount of at least 0.5 percent by weight of the catalyst;
wherein said catalyst produces a reduced amount of polyalkylated products as compared to an identical catalyst not having said amount of metal cation present.

7. The method of claim 6, wherein the monoalkylated aromatic compound is ethylbenzene, the alkylating agent is ethylene, and the aromatic feed is benzene.

8. The method of claim 6, wherein the monoalkylated aromatic compound is cumene, the alkylating agent is propylene, and the aromatic feed is benzene.

9. A method for producing monoalkylated aromatic compounds, comprising the step of contacting an aromatic feed with an alkylating agent in the presence of a catalyst, to produce a monoalkylated aromatic compound and polyalkylated products, said catalyst comprising:
   (a) a MCM-22 molecular sieve; and
   (b) a metal cation of Cu that is present in said catalyst in an amount at least 0.5 percent by weight of the catalyst;
wherein said catalyst produces a reduced amount of polyalkylated products as compared to an identical catalyst not having said amount of metal cation present.

10. The method of claim 9, wherein the monoalkylated aromatic compound is ethylbenzene, the alkylating agent is ethylene, and the aromatic feed is benzene.

11. The method of claim 9, wherein the monoalkylated aromatic compound is cumene, the alkylating agent is propylene, and the aromatic feed is benzene.

12. A method for producing monoalkylated aromatic compounds, comprising the step of contacting an aromatic feed with an alkylating agent in the presence of a catalyst, to produce a monoalkylated aromatic compound and polyalkylated products, said catalyst comprising:
   (a) a MCM-22 molecular sieve; and
   (b) at least one metal cation selected from Al, Ce, Ga, K, La, Mg, Mo, Zn and Zr, said metal cation present in said catalyst in an amount of at least 0.5 percent by weight of the catalyst;
wherein said catalyst produces a reduced amount of polyalkylated products as compared to an identical catalyst not having said amount of metal cation present.

13. The method of claim 12, wherein the monoalkylated aromatic compound is ethylbenzene, the alkylating agent is ethylene, and the aromatic feed is benzene.

14. The method of claim 12, wherein the monoalkylated aromatic compound is cumene, the alkylating agent is propylene, and the aromatic feed is benzene.

15. The method of any of the preceding claims, wherein said contacting is conducted at a temperature of from about 0° C. to about 500° C., a pressure of from about 0.2 to about 250 atmospheres (20 to 25250 kPa), a molar ratio of aromatic feed to alkylating agent of from about 0.1:1 to about 50:1, and a feed weight hourly space velocity of from about 0.1 and about 500 $hr^{-1}$.

* * * * *